United States Patent [19]

Lesser

[11] 4,345,466
[45] Aug. 24, 1982

[54] APPARATUS FOR OBTAINING SAMPLES AT VARIOUS LEVELS FROM WITHIN A MULTI-LIQUID CONTAINER PRIMARILY FOR DETERMINING THE LEVEL OF THE LIQUID INTERFACE AND RELATED METHOD

[76] Inventor: N. Lewis Lesser, 536 Ridgewood Ave., Glen Ridge, N.J. 07028

[21] Appl. No.: 105,564

[22] Filed: Dec. 20, 1979

[51] Int. Cl.³ .............................................. G01F 23/04
[52] U.S. Cl. .................................... 73/298; 73/863.82
[58] Field of Search ............... 73/298, 425.4 R, 425.6, 73/863.82, 864.34, 864.73

[56] References Cited

U.S. PATENT DOCUMENTS

| | | | |
|---|---|---|---|
| 455,733 | 7/1891 | Bell | 73/425.4 R |
| 1,527,099 | 2/1925 | Wilcox | 73/425.6 X |
| 2,014,739 | 9/1935 | Knight | 73/298 |
| 3,250,122 | 5/1966 | Doering | 73/298 |
| 4,196,627 | 4/1980 | Locher | 73/425.4 X |

Primary Examiner—James J. Gill
Attorney, Agent, or Firm—Gottlieb, Rackman & Reisman

[57] ABSTRACT

An apparatus and related method for obtaining samples from within a multiple liquid container, e.g. a tank within an oil tanker, at various levels in such container and for determining the level of the interface of the different liquids in such container. The apparatus operates in cooperation with a sampling bob which can obtain liquid samples from within the tank, at whatever level it is located. The apparatus is attachable to a hatch which leads into the tank, and initially fixes the level at which the sampling bob takes a sample, usually at the tank bottom. Then, the apparatus enables the sampling bob to be shifted to a different level by movement of a positioning slide through a measured interval, so that the sampling bob can take a sample at this second level. Continued sampling at different levels enables the user to determine the location of the interface of two liquids, such as oil and water, in such a container.

19 Claims, 8 Drawing Figures

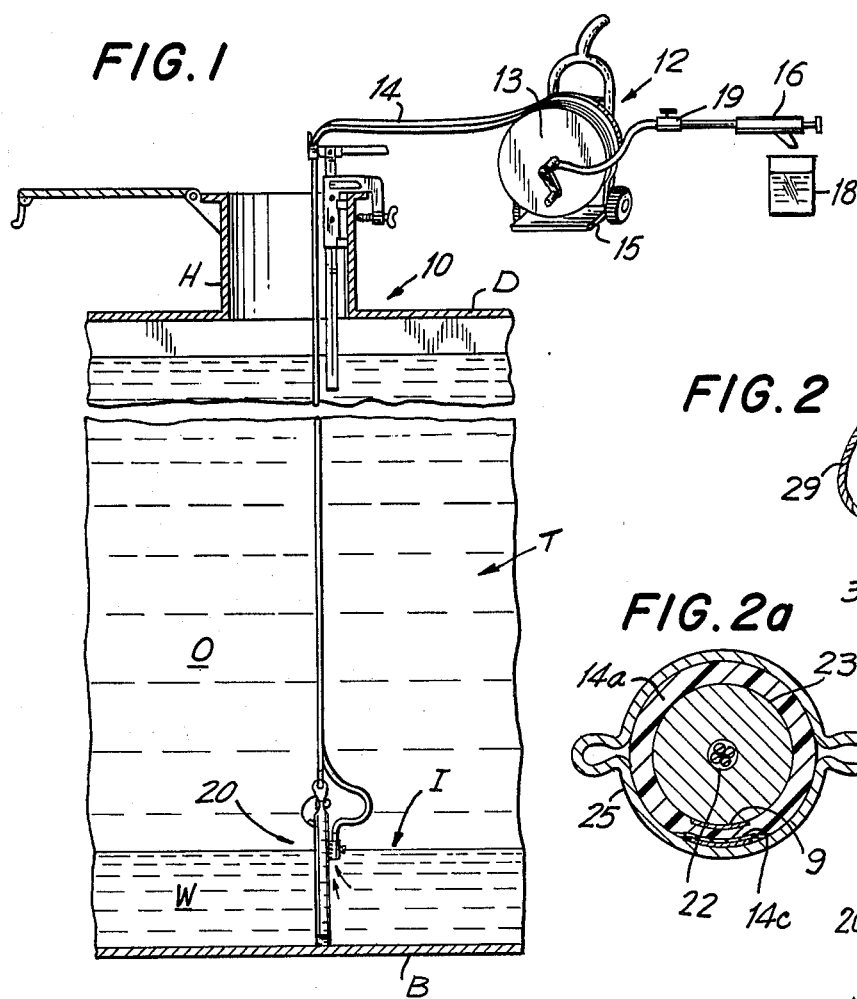
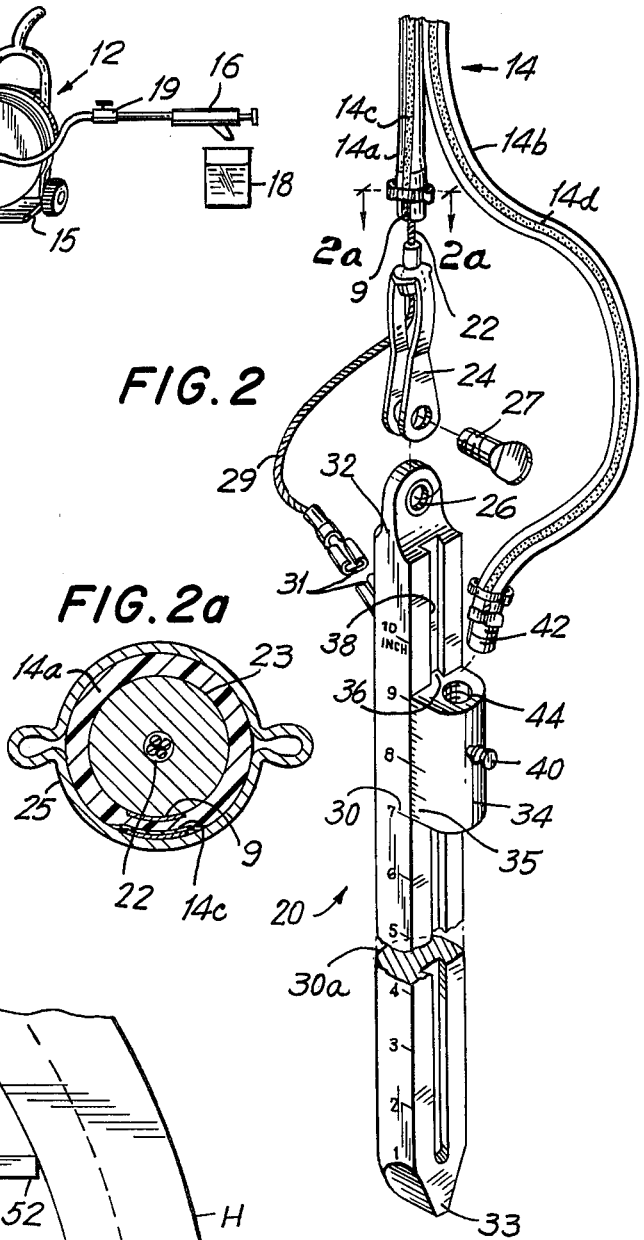
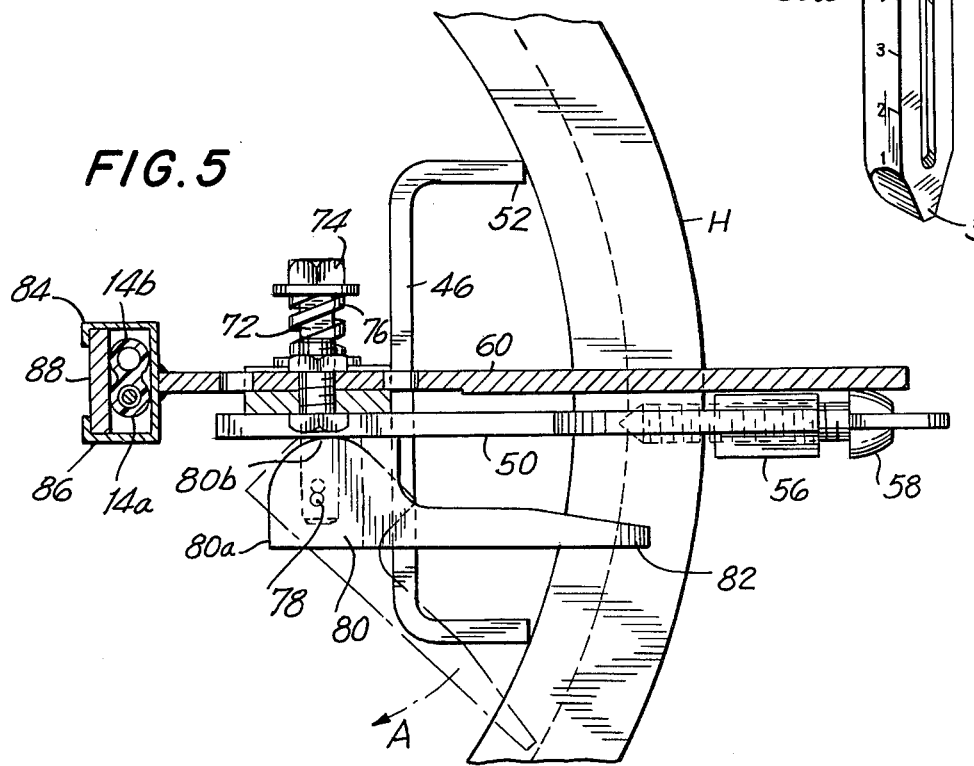

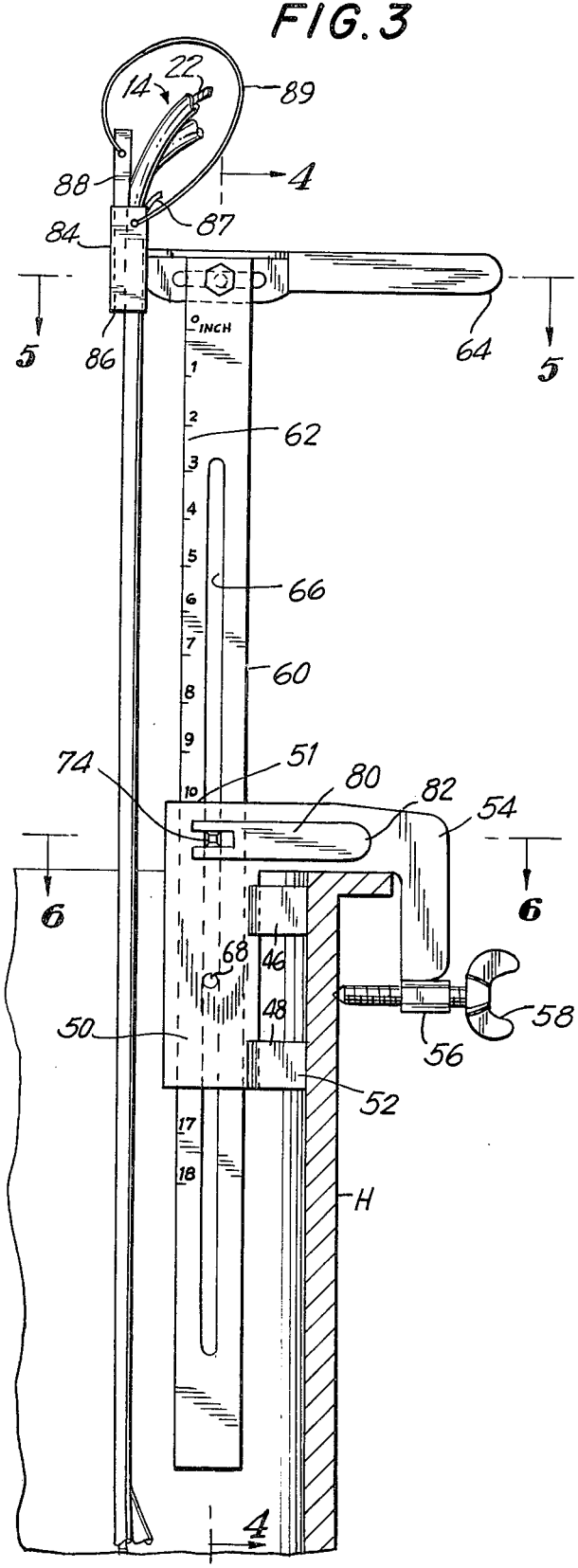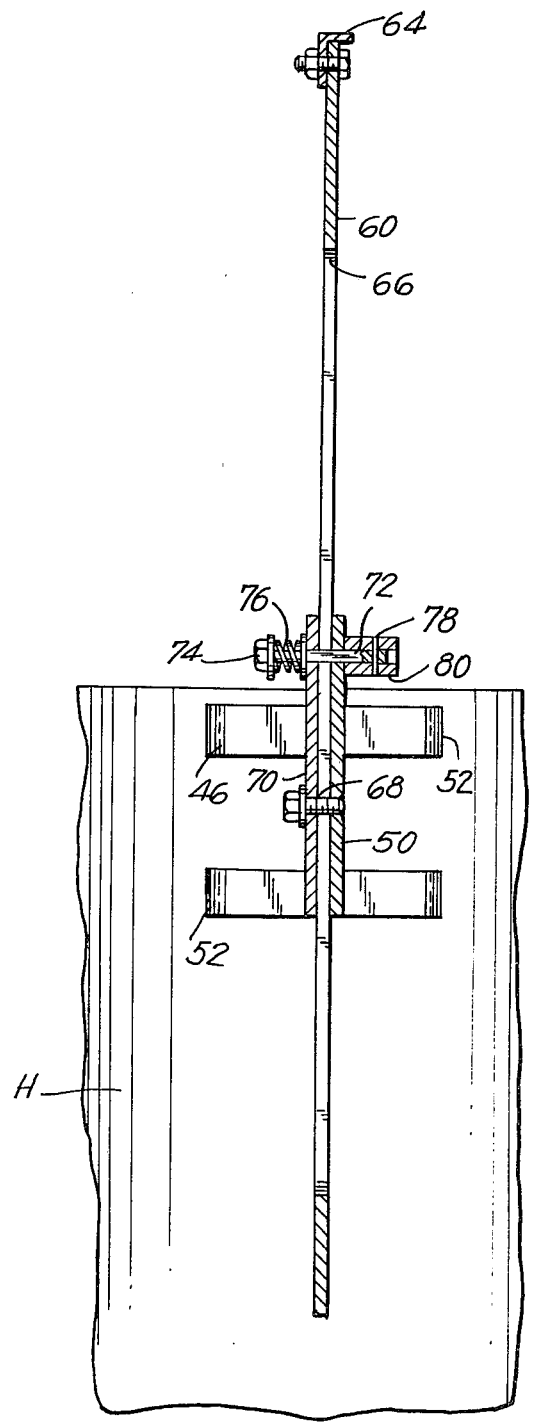

APPARATUS FOR OBTAINING SAMPLES AT VARIOUS LEVELS FROM WITHIN A MULTI-LIQUID CONTAINER PRIMARILY FOR DETERMINING THE LEVEL OF THE LIQUID INTERFACE AND RELATED METHOD

BACKGROUND OF THE INVENTION

The present invention relates to an apparatus and method for obtaining samples at different levels from within oil containers such as an oil storage tank or a cargo tank of an oil tanker, in order to accurately determine the level of water in such a tank, the remainder of the tank being filled with oil and thereby to determine the level of the water/oil interface therein.

It often occurs that oil which is loaded into oil tanks of oil tankers at ports contains substantial quantities of water. This is because water was produced or obtained during the oil drilling process, and was loaded aboard the tanker along with the crude oil. Also, water may already be within such a cargo tank, because of leakage into the tanks or because the water was inadvertently left in the tanks when the tanks were filled with sea water which was used for ballast.

The purchaser of such oil loaded aboard a tanker wishes to determine the exact quantity of water within a tank otherwise filled with oil, and wishes to determine the chemical nature of the water, which may be determined by taking a sample of such water. A determination of the nature of such water will help determine its source. Furthermore, such a buyer may be required to pay only for the oil placed aboard the tanker and not the water, and the transporter of the oil cargo may desire to check such tanks himself. Hence, accurate water-oil interface determinations in such tanks are likely to be economically valuable.

It is already known in this art to lower a sampling bob to the bottom of the liquid-filled tank, either a storage tank or within an oil tanker, to obtain samples of such liquids at various levels, and thereafter to test such samples to determine whether at any given level, water or oil is present. However, the art requires an apparatus and method for utilizing such bobs to determine water levels in such tanks quickly and efficiently and in a manner so that the results are reliable, and requires improved sampling bobs for use with such apparatus. Patent application Ser. No. 937,293, filed Aug. 28, 1978, entitled "Method And Apparatus For Obtaining A Selective Liquid Sample From Near The Bottom Surface Of A Liquid-Filled Tank", assigned to Mobil Oil Corporation, shows a prior sampling bob and system.

SUMMARY OF THE PRESENT INVENTION

The present invention provides a readily operable apparatus and related method for cooperating with an improved sampling bob so that the level of the oil/water interface within the oil tank can be quickly determined, whereupon calculations can be made to determine the quantity of oil, the quantity of water and the nature of the water within the tank.

The sampling bob is attached to a tube that runs from the bob upwardly through the hatch or other passageway of the tank and to a testing location on the deck of the tanker. A suction pump at the upper end of the tube enables a sample to be taken by the bob at whatever level the bob is located.

The sampling apparatus includes means for attaching it quickly to the hatch which leads into the oil tank. The tube, used for sampling purposes, passes through the apparatus to the sampling bob. The bob, connected to the end of the tube, is lowered to the bottom of the tank, and then the tube is fixed in place relative to the apparatus. A sample is then taken to determine whether oil or water is present at the level of the bob at that time, that is, at the bottom of the tank. Then, through use of a positioning slide in the apparatus, the tube is raised a determined interval, and then again is fixed in place, thereby raising the sampling bob the same interval. Through this action, the nature of the liquid at the second level can be sampled. The apparatus is continuously operated in a similar manner to take samples at different levels, until a sample is taken of water below the oil/water interface and until a sample of oil is taken above the oil/water interface, so that a precise determination can be made of the location of such interface.

BRIEF DESCRIPTION OF THE DRAWINGS

The construction and operation of the present apparatus and sampling bob will be better understood by reference to the following drawings, wherein:

FIG. 1 is a side elevational view of the apparatus for obtaining samples at various levels from within a multi-liquid container in order to determine the liquid interface level therein, showing such apparatus in operation with an oil tank in an oil tanker;

FIG. 2 is a perspective view of an improved sampling bob utilized with said apparatus;

FIG. 2A is a cross-sectional view of the bob tube, taken substantially along the line 2A—2A of FIG. 2;

FIG. 3 is a side elevational view of the apparatus enlarged as compared to the view of FIG. 1;

FIG. 4 is a vertical cross-sectional view of the apparatus taken substantially along the line 4—4 of FIG. 3;

FIG. 5 is a horizontal cross-sectional view taken substantially along the line 5—5 of FIG. 3;

DETAILED DESCRIPTION OF THE STRUCTURE OF THE APPARATUS

Figure 6:
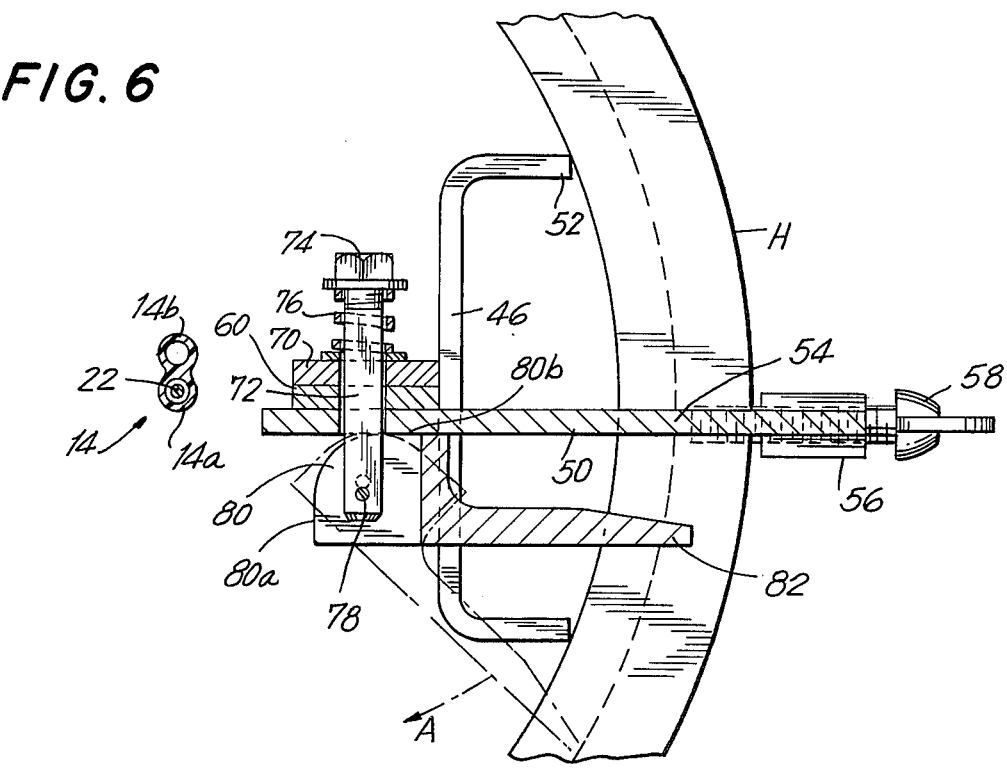
FIG. 6 is a horizontal cross-sectional view taken substantially along the line 6—6 of FIG. 3.

In accordance with the objects of my invention, there is provided an apparatus, generally 10, which enables a user to obtain samples of liquid at selected levels within a multi-liquid container so as to determine the liquid interface level therein. The apparatus is used with a reel assembly 12 which can wind or unwind, as desired, a twin or "figure 8" tube 14 through which the liquid sample passes. The reel assembly 12 is portable and includes a reel 13 on which tubing can be wound, and a cart 15, for mounting the reel. The reel is connected to ground.

The tube 14, beyond the reel 13, is attached through a connector 19 to a conventional suction pump 16, which can draw liquid up the tube 14 and dispense it into a container 18 for observation and testing purposes. The pump may be of the type manufactured by ITT-Jabsco Products of Costa Mesa, Calif.

The tube 14 at its lower end is attached to a sampling bob 20, shown best in FIG. 2. The tube 14 may be comprised of a soft, heat resistant thick-walled, clear plastic, such as ethyl-vinyl-acetate, cross linked through radiation. Such tube may have a conductive "stripe" for grounding purposes.

The tube 14, being of "figure 8" configuration, is made up of two separate, parallel passages 14a, 14b. Passage 14b provides a passageway through which the liquid sample is taken from the liquid container and is of relatively small internal diameter, e.g. of one-quarter inch internal diameter. The wall thickness of passage 14b is sufficient so that it is highly resistant to collapsing under low-pressure conditions, that is, when the pressure internally of the passage is less than the pressure of liquid external to it, as would happen when pump 16 is operated. Passage 14b may carry a conductive "stripe" 14d for grounding purposes.

Line 22 is positioned within and through the other passage in tube 14, passage 14a, and is gripped by a tube slug 23 which closes the lower end of tube 14a. A clamp 25 fixes the slug 23 in place within the lower end of tube 14a. A U-shaped clip 9, see FIG. 2a, conductively connects the slug 23 to the conductive stripe 14c.

The line 22 next engages a clevis 24, which in turn, carries a locking pin 27. The pin 27 passes through an aperture 26 at the upper end 32 of the sampling bob 20. The line 22 is desirably made of a flexible stainless steel, so that it and the tube 14a may both support the bob 20 for purposes of raising and lowering it and may provide an electrical conduit via line extension 29 and connectors 31 for grounding of the bob 20 to the reel assembly 12 for safety purposes. In turn, the reel assembly 12 will be grounded to a portion of the tank, so that the use of the bob will be safe within an otherwise hazardous environment which may include explosive atmospheres.

The sampling bob 20, improved as compared to those known in the art, is formed of brass or other heavy, "soft", liquid-resistant metal or other like material, and is especially adapted for being lowered to the bottom of an oil-filled tank. The bob is calibrated on one or more of its elongated sides, as shown at 30, with a calibration running from a zero point at the lower wedge end or tip 33 of the bob and running upwardly along the length of the bob to a point adjacent the upper end 32 of the bob.

A slide 34, also calibrated as at 35, is mounted on one side of the bob 20, and is adapted for being positioned at various points along the length of the bob. The slide 34 is a hollow, somewhat cylindrical member with an axial bore 44, and has a projecting key 36 which mates into a 60° dovetail slot 38, which runs along the length of the bob, thereby enabling the slide to move along the slot 38 and therefore along the length of the bob. A set screw 40 in the slide, when tightened, fixes the location of the slide 34 in the guideway 38.

The lowermost end of the passage 14b, through which liquid passes, terminates in a threaded sleeve 42, which engages the upper end of the bore 44 in the slide 34. The bore 44 passes through the slide 34 and is slightly enlarged through the lower three-quarters of its length so as to prevent a vortexing effect, when liquid is drawn first into the slide 34 and then into the passage 14b. The conductive stripe 14d in passage 14b is connected to the slide 34 through a clip and clamp similar to that used on passage 14a.

The apparatus 10 cooperates with the bob 20 and is adopted for use with a liquid-filled tank T, formed by a top wall or deck D and a tank bottom B, with the tank having a hatch or passageway H, by which the tank can be entered. In the tank will usually be a major liquid portion which is oil O, and a minor liquid which is water W, forming an oil/water interface I, see FIG. 1.

The apparatus includes means for securely, but removably, clamping it to the hatch H. The clamp means, best shown in FIGS. 3-7, includes a pair of C braces, namely an upper C brace 46 and a lower C brace 48. The braces 46, 48 are substantially identical and are similarly oriented. The pair of C braces 46, 48 are held rigidly by a frame 50, see FIGS. 6 and 7, which holds the brace members so that their tips 52 abut against the inside face of the wall of the hatch H. An arm 54 of L configuration is attached to and extends from the frame 50, and carries at its lower end an internally-threaded nut or band 56, see FIG. 3. A headed locking screw 58, which can also serve as a grounding member, engages the band 56 and can be manually rotated so as to press firmly against the external face of the wall of the hatch H, and through any paint on the hatch, to make good contact. When the locking screw 58 is rotated so that it travels toward the hatch wall, it forces the C braces 46, 48 against the internal face of the hatch wall, thereby securely fixing the frame relative to the hatch.

The apparatus 10 also includes a linear-positioning slide 60. The slide 60, of rectangular shape and elongated in a vertical direction, has one or several scales 62 along its sides. The positioning slide 60 has a handle 64 fixed to its upper end, so that a user may readily grasp it and assert upward or downward pressure on the positioning bar.

The slide 60 has an elongated slot 66 formed along its long axis, the slot being closed at both of its ends. Spaced pins passing through the slot 66 enable the positioning slide 60 to move upwardly and downwardly relative to the frame 50. To this end, a lower pin 68 passes from the frame 50 through the slot 66 in the positioning slide 60 and into a member parallel to the frame, a brake 70, and causes a noninterference fit between these parts. An upper pin 72, to be described in further detail subsequently, also passes from the frame 50 through the slot 66 in the slide 60 and into the brake 70. The pins 68, 72, passing through the slot 66 in the positioning slide 60, guide the upward and downward movement of the positioning slide along a vertical line, indicated by the arrows D shown in FIG. 7.

The positioning slide 60 can be temporarily retained in place in relation to the frame by brake means. The brake means includes the brake 70 and cam means for forcing the brake 70 against the positioning slide 60. As shown in FIG. 6, the positioning slide 60 is sandwiched between the parallel frame 50 and the brake 70, with upper pin 72 passing through all three of these members. The pin 72 extends on both of its ends, on one side beyond brake 70 and on the other side beyond frame 50, as shown in FIGS. 4 and 6. On the end of pin 72 which passes through brake 70, a threaded stop nut 74 is engaged, and a spring 76 on the same pin end is situated between the stop nut 74 and the brake 70. The spring tends to move the brake 70 toward the positioning slide 60.

The other end of the upper pin 72, that is, the end which protrudes through frame 50, terminates by carrying a pivot pin 78, on which a cam segment 80 connected to a handle 82 is mounted for rotation. The cam segment 80 includes curved sector 80a and connecting curved section 80b, sector 80b having a larger radius than sector 80a. As will be seen in FIGS. 5, 6 and 7, when the handle 82 is rotated in the direction A to open the brake, the cam segment 80 is also rotated, so that segment 80a contacts frame 50 rather than segment 80b, thereby enabling the upper pin 72 to shift toward brake 70, in turn allowing the spring 76 to expand and to cause less pressure to be exerted by the spring on the brake 70 and the brake 70 on the slide 60. With this slack, the positioning slide 60 is no longer held stiffly in place by the brake 70 and can then be urged to slide upwardly and downwardly, to the degree desired. As mentioned previously, this upward and downward movement of the positioning slide 60 is controlled by the application of force to handle 64.

One end of handle 64 carries a tube wedge mechanism 84. Specifically, an open, relatively short, vertically-oriented channel 86 with a curved tube guide 87 is fixed to one end of handle 64, the end which would overhang the hatch H, and comprises an open-ended passage in which the tube 14 may be readily placed. When it is desired to fix the tube 14 relative to the channel 86, a metal wedge 88 is slipped into the channel 86, thereby wedging the tube 14 against the back wall of the channel 86, and thereby holding the tube in a fixed position relative to the apparatus. The wedge 88 is attached by a tether 89 to the channel 86.

DESCRIPTION OF OPERATION OF APPARATUS AND METHOD

The apparatus is utilized in accordance with the following method. First, the sampling bob is prepared for use, by placing the locking pin 27 of clevis 24 on line 22 through the aperture 26 at the upper end 32 of the bob, attaching the line extension 29 to the bob via connectors 31 for grounding purposes, and having the sleeve 42 at the end of passage 14b threaded into the slide 34. The bottom edge of slide 34 is positioned at a relatively low point on the bob, e.g. next to number 1 on scale 30 is fixed in place by tightening the set screw 40.

The initial position of the slide 34 with respect to the bob 20 is determined through experience in such sampling operations. This position is usually low on the bob, but not at the very bottom of the bob. This is because there is usually a thick sludge at the bottom of the oil tank, which might clog the bore 44 in the slide 34, if the slide were at the very bottom of the bob.

On occasion, a water-activated, "paste" which is sensitive to water but not to oil, is applied to the rounded face 30a of the sampling bob, for purposes of making an initial determination of the oil/water interface level. This determination will usually yield a rough estimate of this level, which is subject to a more accurate determination by the apparatus and method of the present application.

The apparatus 10 is fixed to the hatch H which leads into the tank T by locating the same so that the C braces 46, 48 are located inside of the hatch, and then the locking screw 58 is tightened so that it is forced into the outside of the hatch H. This firmly attaches the apparatus to the hatch H, with the wedge mechanism overlying the hatch opening. The scale 62 on slide 60 is set at the same number with respect to the guide 51, as is the setting of the slide 34 on the bob 20.

The reel assembly 12 is then grounded and the tube may be primed with water. The reel is next unrolled so that the tube 14, at whose end the bob is located, pays out, and the tube and bob pass down into the tank. The reel 12 is continuously unrolled, paying out the tube 14 so as to lower the sampling bob 20 into the tank and into the oil O portion thereof, this lowering step continuing until the lower tip 33 of the bob touches the bottom B of the tank. This can be determined, because when the bob 20 touches bottom B, this can be "felt" in the apparatus.

Then, the tube 14 is secured to the apparatus, by the placement of the tube into the channel 86 and by the placement of the wedge 88 downwardly into the channel 86, wedging and holding the tube in place relative to the apparatus, and also temporarily fixing the level of the bob at the bottom of the tank.

A view of the guide 51 with respect to the scale 62 on slide 60 will indicate a measurement, 1", which is the level of the slide 34 on the bob 20, above the bottom of the oil tank.

At this point, the pump 16 is operated so that the priming liquid is evacuated and liquid located at the level of the slide 34 is sucked into the bore in the slide and up the passage 14b to the pump 16, and thereafter into the container 18. When a sufficient volume of liquid has been drawn into the container 18, sufficient so that liquid at the slide will reach the container 18, the container is taken and the contents thereof are observed to see if oil or water is present at the slide 34.

The apparatus 10 then continues to be used to attempt to determine the level of the oil/water interface I. The positioning slide 60 during this time period had been fixed in place relative to the frame 50, because the cam segment handle 82 had been closed by having been moved in a direction opposite to the arrow A, thereby tightening the brake 70 against the slide 60.

Figure 7:
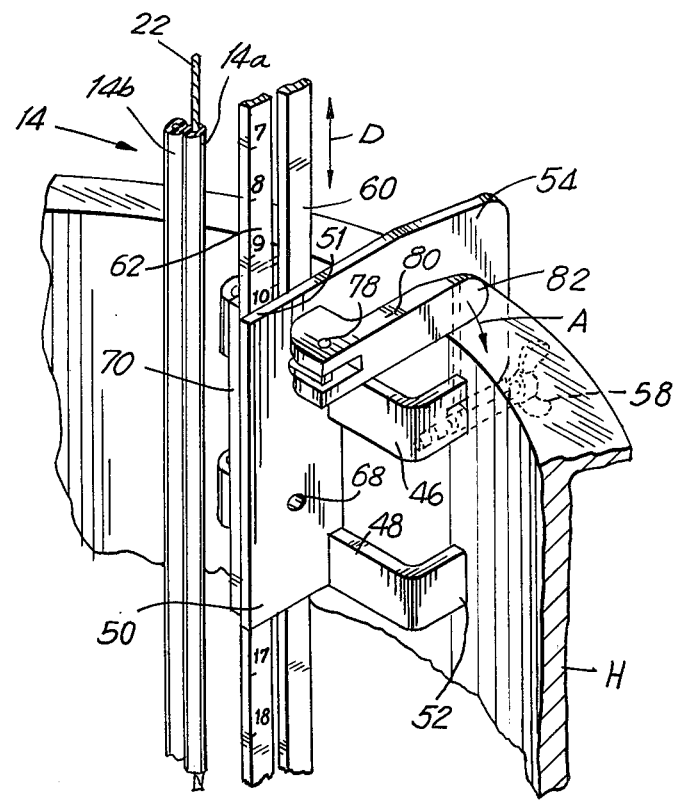
FIG. 7 is a partial perspective view of the brake means of the apparatus.

The handle 82 is now opened by being moved in the direction of the arrow A, swinging the cam segment 80 and thereby loosening the positioning slide 60 so as to permit linear movement. Assuming, as is conventionally the case, that water has been found at the first sampling, the positioning slide 60 is moved upwardly, by grasping the handle 64, and pulling the same upwardly. The degree of upward movement can be measured by a visual observation of the scale 62 on the bar 60. The upper edge 51 of the frame 50, see FIG. 7, is used as a guide for this purpose. For example, the handle 64 and the slide 60, having been set at 1", may be moved upwardly 1 inch, so as to reach the 2" setting. As the slide 60 moves upwardly, the tube 14 is moved upwardly to the same extent, since the tube by virtue of the wedge 84 is fixed relative to the slide 60. Upward movement of the tube 14 to a given extent, e.g. 1", moves the bob 20, carried by line 20, upwards to the same extent, 1". Thus, the slide 34 on the bob 20, having previously been set at 1" on the bob, and therefore having sampled at a level 1" above the tank bottom, is then at a level 2" above the tank bottom.

At this point, with the upward movement having been completed, the handle 82 is moved in a direction opposite to the direction indicated by the arrow A, again clamping the positioning bar 60 in place. The pump 16 is operated again, taking another liquid sample at the level at which the slide 34 is now situated, e.g. 2" above the bottom B of the tank. Again, the pump is operated to obtain a sample to determine whether water or oil is present at this second position of the slide.

This process is continued, the bob and slide being moved upwardly to different levels, usually in one inch increments, until a sample is taken by the slide which shows that the slide is in the oil portion O of the tank. Then, further adjustments of the positioning bar 60 can be made, downwardly or upwardly, usually in $\frac{1}{2}$" or $\frac{1}{4}$" segments, until a relatively exact determination can be made of the level of the oil/water interface I. Once the level of this interface I is determined, conventional calculations can be made to determine the quantity of oil, the quantity of water and the nature of such water, within the tank T. The wedge 88 can now be removed from the channel 86, the tube 14 taken out of the channel, the bob 20 reeled out of the tank by reel assembly 12, and the apparatus 10 disassembled from hatch H.

Thus it will be seen that an apparatus has been provided which enables a user in a quick and efficient manner to determine the location of the oil/water interface in a tank of an oil tanker, so as to readily determine the quantity of oil that has been placed aboard a tanker at dockside. While an oil tank has been given as an example, it will be apparent that the apparatus and the related method can sample liquids and determine the levels of liquid interfaces in any type of container, with any number of different liquids being in the tank.

What I claim is:

1. An apparatus for determining the level of the liquid interface from within a multi-liquid container having a passageway leading therein, said apparatus being adapted for use with a sampling bob connected by a flexible tube to an elevated location with respect to such container, said apparatus comprising:
   (a) a frame,
   (b) clamp means for removably attaching the frame to the container,
   (c) positioning means slidably mounted for vertical movement relative to the frame,
   (d) means for temporarily fixing the sampling bob tube at any point along a substantial portion of its length to the positioning means, and
   (e) means on the frame for retaining the positioning means at various vertically spaced locations,
whereby, when the positioning means is shifted to various vertically spaced locations, the sampling bob is similarly shifted to various vertically spaced locations through substantially the entire height of the container.

2. An apparatus as set forth in claim 1 wherein the clamp means comprises at least one "C"-shaped member, a locking screw and means for permitting movement of the screw toward the C-shaped member.

3. An apparatus as set forth in claim 1 wherein the positioning means comprises an elongated slide, an elongated slot in the slide, and pin means passing from the frame through the slot.

4. An apparatus as set forth in claim 1 wherein a handle is carried by the positioning means for manual movement thereof.

5. An apparatus as set forth in claim 3 wherein the retaining means comprises a brake, and cam means mounted for rotational movement on the frame for urging the brake into contact with the slide.

6. An apparatus as set forth in claim 1 wherein the clamp means comprises at least one "C"-shaped member, a locking screw and means for permitting movement of the screw toward the C-shaped member and wherein the positioning means comprises an elongated slide, an elongated slot in the slide, and pin means passing from the frame through the slot.

7. An apparatus as set forth in claim 1 wherein the retaining means comprises a brake and cam means mounted on the frame for urging the brake into contact with the positioning means.

8. An apparatus as set forth in claim 3 wherein a handle is carried by the slide, for manual movement thereof.

9. An apparatus as set forth in claim 1 wherein the fixing means comprises a channel attached to the positioning means in which the tube can be received, and a wedge insertable into said channel.

10. An apparatus as set forth in claim 9 wherein the channel is located over the passageway when the clamp means is attached adjacent the passageway.

11. An apparatus as set forth in claim 1 further including pump means for drawing liquid samples through the sampling bob.

12. An apparatus for determining the level of the liquid interface from within a multi-liquid container, said apparatus being adapted for use with a sampling bob connected by an elongated flexible member to an elevated location with respect to such container, said apparatus comprising:
   (a) a frame,
   (b) clamp means for attaching the frame adjacent to a passageway leading into the container,
   (c) positioning means slidably mounted for vertical movement relative to the frame, said positioning means comprising an elongated slide, an elongated slot in the slide, and pin means passing from the frame through the slot,
   (d) means for temporarily fixing the flexible member leading to the sampling bob to the positioning means, and
   (e) means on the frame for retaining the positioning means at various vertically spaced locations, said retaining means comprising a brake and cam means mounted for rotational movement on the frame for urging the brake into contact with the slide, the pin means passing from the brake through the slot and to the frame,
whereby, when the positioning means is shifted to various vertically spaced locations, the sampling bob is similarly shifted to various vertically spaced locations within the container.

13. An apparatus as set forth in claim 12 wherein the flexible member comprises an elongated line.

14. In combination, an apparatus for obtaining samples at various levels from within a multi-liquid container to determine the liquid interface level therein, and a sampling bob connected by a tube to an elevated location with respect to such container, said sampling bob including:
   (a) a slide having a through-bore therein, said bore being connected to the tube, and
   (b) means for mounting the slide for movement along the bob,
said apparatus comprising:
   (c) a frame,
   (d) clamp means for attaching the frame to the container,
   (e) positioning means slidably mounted for vertical movement relative to the frame, said positioning means comprising an elongated slide, an elongated slot in the slide, and pin means passing from the frame through the slot,
   (f) means for temporarily fixing the tube leading to the sampling bob to the positioning means, and
   (g) means on the frame for retaining the positioning means at various vertically spaced locations, said retaining means comprising a brake and cam means mounted for rotational movement on the frame for urging the brake into contact with the slide, the pin means passing from the brake through the slot and to the frame,
whereby, when the positioning means is shifted to various vertically spaced locations, the slide on the sampling bob is similarly shifted to the same extent to various vertically spaced locations within the container.

15. A sampling bob for use in obtaining samples at various levels from within a multi-liquid container to determine interface level therein, the bob being connected by a tube to an elevated location with respect to such container, the bob including:
   (a) a slide having a bore therein, said bore being connected to the tube and
   (b) means for mounting the slide for movement along the bob.

16. A sampling bob as set forth in claim 15, wherein the slide has a scale thereon and the bob has a scale thereon, the scales being adjacent.

17. A sampling bob as set forth in claim 15, wherein the bob comprises an elongated, heavy, water-resistant member having a slot therein, and wherein the slide has a projection slidable in said slot.

18. An apparatus for determining the level of the liquid interface from within a multi-liquid container, said apparatus being adapted for use with a sampling bob connected by a tube to an elevated location with respect to such container, said apparatus comprising:
   (a) a frame,
   (b) clamp means for attaching the frame to the container,
   (c) positioning means slidably mounted for vertical movement relative to the frame, said positioning means comprising an elongated slide, an elongated slot in the slide, and pin means passing from the frame through the slot,
   (d) means for temporarily fixing the sampling bob tube to the positioning means, and
   (e) means on the frame for retaining the positioning means at various vertically spaced locations, said retaining means comprising a brake and cam means mounted for rotational movement on the frame for urging the brake into contact with the slide, the pin means passing from the brake through the slot and to the frame, whereby, when the positioning means is shifted to various vertically spaced locations, the sampling bob is similarly shifted to various vertically spaced locations within the container.

19. A method for obtaining samples of liquids at various levels from within a multi-liquid filled container to determine the liquid interface level therein, said method comprising the steps of:
   (a) locating a slide carried on a sampling bob in a given relation,
   (b) lowering the sampling bob, connected by a tube to an elevated location with respect to such container, to the bottom of such container,
   (c) fixing said tube to a slidable member at said elevated location,
   (d) locating the slidable member relative to the elevated location in the same given relation as the slide to the bob,
   (e) withdrawing the liquid in the tube by means of a pump, so as to determine the nature of the liquid at the level of the bob,
   (f) moving the slidable member vertically to a specified extent to a second level, whereby the sampling bob will move within the container to a like extent,
   (g) taking an additional sample at the second level of the sampling bob, and
   (h) continuing such sampling procedures at various levels within such container to determine the level of interface of two different liquids within such container.

* * * * *